United States Patent [19]

Schwartz

[11] Patent Number: 5,658,558
[45] Date of Patent: Aug. 19, 1997

[54] HAIR STYLING COMPOSITIONS AND METHOD OF ENHANCING THE PERFORMANCE OF HAIR FIXATIVE RESINS

[75] Inventor: Curtis Schwartz, Ambler, Pa.

[73] Assignee: Rohm and Haas Company, Philadelphia, Pa.

[21] Appl. No.: 437,449

[22] Filed: May 8, 1995

Related U.S. Application Data

[63] Continuation-in-part of Ser. No. 316,008, Oct. 3, 1994, abandoned.

[51] Int. Cl.$^6$ .............................. A61K 7/06; A61K 7/11
[52] U.S. Cl. .................. 424/70.16; 424/70.12; 424/47
[58] Field of Search .................. 424/70.16, 70.11, 424/70.12, 47

[56] References Cited

U.S. PATENT DOCUMENTS

| | | |
|---|---|---|
| 4,196,190 | 4/1980 | Gehman et al. . |
| 4,289,752 | 9/1981 | Mahieu et al. . |
| 4,786,493 | 11/1988 | Smith et al. . |
| 4,847,076 | 7/1989 | Deshpande et al. . |
| 4,983,618 | 1/1991 | Pulido et al. . |
| 5,116,601 | 5/1992 | Mondet et al. . |
| 5,160,729 | 11/1992 | Login et al. . |
| 5,164,177 | 11/1992 | Bhatt et al. . |
| 5,176,898 | 1/1993 | Goldberg et al. . |
| 5,182,098 | 1/1993 | Kopolow et al. . |
| 5,196,495 | 3/1993 | Chuang et al. . |
| 5,206,009 | 4/1993 | Watling et al. . |
| 5,223,247 | 6/1993 | Kopolow et al. . |
| 5,277,899 | 1/1994 | McCall . |
| 5,294,437 | 3/1994 | Shah et al. . |
| 5,314,684 | 5/1994 | Horoschak et al. . |
| 5,332,765 | 7/1994 | Lorentzen et al. . |

FOREIGN PATENT DOCUMENTS

| | | |
|---|---|---|
| 551748 | 12/1992 | European Pat. Off. . |
| 551749 | 12/1992 | European Pat. Off. . |
| 590604 | 9/1993 | European Pat. Off. . |
| 635257 | 7/1994 | European Pat. Off. . |
| 2112 | 2/1994 | WIPO . |

OTHER PUBLICATIONS

"Polymer For Low VOC Hairsprays", National Starch and Company, pp. 1 through 18. (no date).
"Acudyne 255, Hair Fixative Polymer for low VOC Hairsprays", Rohm and Haas Company, pp. 1 through 11. 1994.

*Primary Examiner*—Salle M. Gardner
*Attorney, Agent, or Firm*—Kimberly R. Hild

[57] ABSTRACT

The present invention provides aqueous low (70 weight percent or less) VOC hair styling compositions.

More particularly, the present invention provides a low VOC hair styling composition containing at least one acrylic hair fixative resin and one or more plasticizing compounds selected from polycarboxylic acid esters and dimethiconecopolyols.

The present invention also provides a low beading, low VOC hair styling composition comprising at least one surface tension reducing compound, at least one acrylic hair fixative resin, and at least one simethicone.

The present invention also provides an aqueous hair resin composition which inhibits microbial growth. The aqueous hair resin composition contains at least one acrylic hair fixative resin and iodopropynylbutylcarbamate.

15 Claims, No Drawings

HAIR STYLING COMPOSITIONS AND METHOD OF ENHANCING THE PERFORMANCE OF HAIR FIXATIVE RESINS

This is a continuation-in-part of application Ser. No. 08/316,008 filed on Oct. 3, 1994, now abandoned.

BACKGROUND

The present invention relates to hair styling compositions. More particularly, the present invention relates to aqueous hair styling compositions containing low, or 70 weight percent or less volatile organic compounds (VOC). The present invention also relates to a method of enhancing the performance of hair fixative resins by adding certain additives to hair styling compositions.

Hair styling compositions, such as hair sprays, styling gels, spray on gels, and mousses are used on hair to hold the hair in a particular shape or configuration. The hair styling compositions, when applied, form a thin film of hair fixative resin on the hair. This thin film of resin holds adjacent hairs together to retain a particular shape or configuration.

The hair styling compositions can be applied to the hair in several ways. For example, the hair styling composition may be applied by a spray using a propellant, such as in an aerosol hair styling product, or using a hand pump.

Hair styling compositions typically contain one or more volatile organic compounds (VOC). VOC contain at least one carbon atom and are typically used as solvents or propellants in hair styling compositions. VOC contribute to ground level air pollution in the presence of sunlight and air, and are volatile under ambient conditions. VOC include, for example, $C_1$ to $C_{12}$ straight or branched chain alcohols such as methanol, ethanol, propanol, isopropanol, or butanol; $C_1$ to $C_{12}$ straight or branched chain hydrocarbons such as methane, ethane, propane, isopropane, isobutane, pentane, isopentane, or butane; or ethers such as dimethyl ether, or dimethoxymethane.

Recent legislation in New York and California has mandated that the amount of VOC formulated into hair styling compositions that are sprayed, such as hairsprays, must not exceed 80 weight percent in the composition. By 1998, the amount of VOC in hair styling compositions that are sprayed must be reduced to 55 weight percent in California. Other states may enact similar legislation mandating the reduction of VOC in hair styling compositions that are sprayed. Present hair styling compositions which are sprayed typically have equal to or greater than 80 weight percent VOC. The most likely replacement for VOC is water.

The introduction of water into the hair styling composition can adversely affect the performance of the composition. For example, depending on the hair fixative resin and other additives in the composition, water can cause the composition, when sprayed, to form droplets or beads on the hair. These beads leave undesirable visible residue on the hair when dried, and can impart a raspy feel to the hair when combed. Water also has the disadvantage of increasing the drying time of the hair styling composition after it is applied to the hair when compared to hair styling compositions containing higher levels of VOC.

Water can also adversely affect the properties of the hair fixative resin. For example, if the hair fixative resin is water soluble, water can cause high composition viscosities (greater than 15 centipoise) leading to decreased sprayability of the hair styling composition and clogging of the spray nozzle. Water soluble hair fixative resins, when used in low VOC hair styling compositions, are also more likely to become tacky after being applied to the hair. The water soluble hair fixative resins may also have poor curl retention properties due to their inability to dry completely when applied to the hair in a low VOC hair styling composition.

These undesirable properties become particularly severe when the hair styling composition contains about 15 weight percent or more water. As a result, hair styling formulators have begun to redesign their hair styling compositions.

A particular problem in developing a low VOC hair styling composition is finding a suitable plasticizer for the hair fixative resin. The plasticizer gives the hair fixative resin flexibility so that the resin when applied to the hair forms a film, which feels smooth and does not crack or break when combed. The water in a low VOC hair styling composition can adversely affect the plasticizer. For example, the plasticizer in a low VOC hair styling composition, can increase the tackiness, decrease the curl retention, or increase the drying time of the hair fixative resin. The plasticizer may also just be completely ineffective in plasticizing the resin in the presence of water.

Another problem in low VOC hair styling compositions is that the hair fixative resin, prior to being added to the hair styling composition, and the hair styling composition itself may need one or more preservatives to prevent microbial growth. More particularly, hair fixative resins dissolved or suspended in an aqueous composition, hereinafter called the "aqueous hair resin composition" can be inadvertently exposed to microbes such as bacteria, yeast, or molds. If the hair fixative resin supports microbial growth, preservatives will be needed in the aqueous hair resin composition to prevent this growth. The aqueous hair resin composition which needs a preservative may be for example the aqueous composition, such as an emulsion, in which the hair fixative resin is dissolved or suspended in before being added to the aqueous hair styling composition. The aqueous hair resin composition may also be the aqueous hair styling composition. The preservatives, however, added to the aqueous hair resin composition can destabilize the aqueous composition or may impart undesirable properties to the hair styling composition.

U.S. Pat. No. 4,196,190 to Gehman, hereinafter referred to as "Gehman" discloses an acrylic hair fixative resin containing from 10 to 30 weight percent of an alkyl acrylate, from 41 to 60 weight percent of methyl methacrylate, from 5 to 20 weight percent of hydroxyethyl methacrylate, and from 10 to 30 weight percent of methacrylic acid. The Gehman patent, although disclosing that water can be used in a hair styling composition containing the acrylic hair fixative resin, does not disclose or suggest the need for low VOC hair styling compositions. The Gehman patent also does not disclose or suggest how to obtain a low VOC hair styling composition, including methods of overcoming the problems associated with low VOC hair styling compositions.

Some low VOC hair styling compositions have already been developed. For example, U.S. Pat. No. 5,176,898 to Goldberg, et al, hereinafter referred to as "Goldberg" discloses an aqueous hair spray formulation having less than 80 weight percent VOC. The aqueous hair spray formulation contains from 1 to 10 weight percent volatile silicone, preferably cyclomethicone or dimethicone copolyol, from 15 to 40 weight percent water/alcohol solution, from 5 to 60 weight percent propellant, from 1 to 10 weight percent water soluble hair fixative resin, and from 0.05 to 3.0 weight percent neutralizer/plasticizer. The dimethicone copolyol is a surfactant and makes the formulation easier to spray. However, the dimethicone copolyol, being a water soluble surfactant, has the undesirable effect of promoting beading when sprayed on the hair in a low VOC hair styling composition. Beading on the hair has the undesirable effects of leaving visible residue on the hair once dried and making the hair feel raspy when combed.

One problem addressed by the present invention is to provide certain plasticizing compounds which impart flexibility to hair fixative resins but do not adversely affect the tack, curl retention, or drying time of the hair fixative resin in a low VOC hair styling composition.

Another problem addressed by the present invention is to provide certain additives which reduce beading in a sprayable low VOC hair styling composition containing at least one soluble surface tension reducing compound and at least one hair fixative resin. The soluble surface tension reducing compound is any soluble compound which reduces the surface tension between the hair styling composition and the gaseous atmosphere above the hair styling composition. This definition includes for example, surfactants and plasticizers.

Another problem addressed by the present invention is to provide certain preservatives for acrylic hair fixative resins which are compatible with aqueous compositions containing the acrylic hair fixative resins.

STATEMENT OF THE INVENTION

In one embodiment, the present invention provides a low VOC aqueous hair styling composition comprising:

A) from 1 to 15 weight percent of at least one acrylic hair fixative resin wherein the acrylic hair fixative resin comprises from 1) 5 to 95 weight percent of at least one $C_1$ to $C_8$ straight or branched chain alkyl (meth)acrylate monomer, 2) from 2 to 70 weight percent of at least one hydroxyalkyl (meth)acrylate monomer, and 3) from 2 to 50 weight percent of at least one $C_3$ to $C_8$ monoethylenically unsaturated monocarboxylic acid monomer, based on the total weight of monomer; B) from 0 to 10 weight percent of one or more insoluble polyester hair fixative resins; C) from 0.01 to 1.0 weight percent of one or more soluble plasticizing compounds selected from the group consisting of polycarboxylic acid esters and dimethicone copolyols; D) water; and E) 70 weight percent or less of one or more volatile organic compounds.

In another embodiment of the present invention a low beading, low VOC aqueous hair styling composition is also provided comprising: A) from 1 to 15 weight percent of at least one acrylic hair fixative resin; B) from 0.01 to 1 weight percent of at least one soluble surface tension reducing compound; C) from 0.0001 to 0.5 weight percent of at least one simethicone; D) water; and E) 70 weight percent or less of one or more volatile organic compounds.

In another embodiment, the present invention provides an aqueous hair resin composition comprising: iodopropynyl-butylcarbamate; water; and from 1 to 60 weight percent of at least one acrylic hair fixative resin; wherein the acrylic hair fixative resin comprises from 1) 5 to 95 weight percent of at least one $C_1$ to $C_8$ straight or branched chain alkyl (meth)acrylate monomer, 2) from 2 to 70 weight percent of at least one hydroxyalkyl (meth)acrylate monomer, and 3) from 2 to 50 weight percent of at least one $C_3$ to $C_8$ monoethylenically unsaturated monocarboxylic acid monomer, based on the total weight of monomer.

DETAILED DESCRIPTION

By a "aqueous hair styling composition" I mean a hair spray, styling gel, spray on gel, or mousse which is used on hair to hold the hair in a particular shape or configuration. Preferably, the aqueous hair styling composition in the present invention is a hair spray.

The aqueous hair styling composition preferably contains 15 to 98 weight percent water, more preferably from 25 to 70 weight percent water, based on the total weight of the aqueous hair styling composition. By "low VOC" I mean the hair styling composition contains 70 weight percent or less volatile organic compounds. Preferably the hair styling composition contains 55 weight percent or less VOC and more preferably contains 40 weight percent or less VOC.

When the word "soluble" is used to describe a compound, such as for example "soluble plasticizing compound", I mean that the compound described is soluble in the low VOC aqueous hairstyling composition. When the word "insoluble" is used to describe a compound, such as for example the "insoluble polyester hair fixative resin," I mean that the compound described is insoluble and dispersed in the low VOC aqueous hairstyling composition.

The term "(meth)acrylate" means methacrylate or acrylate. The term "(meth)acrylic acid" means methacrylic acid or acrylic acid.

In one embodiment of the present invention, a low VOC aqueous hair styling composition containing one or more plasticizing compounds and at least one acrylic hair fixative resin is provided. A method has also been provided for plasticizing the acrylic hair fixative resin in the low VOC aqueous hair styling composition by adding one or more plasticizing compounds to the low VOC aqueous hair styling composition.

The plasticizing compounds enhance the performance properties of the hair fixative in several ways. The ways in which the performance properties of the hair fixative resin are enhanced by the plasticizing compounds include: providing flexibility to the hair fixative resin; imparting a feel of smoothness and softness to the hair, improving the ease of combing; and preventing the film of hair fixative resin on the hair from cracking or breaking.

The plasticizing compounds which have been found to be effective in the present invention are of two classes of compounds. The first class of plasticizing compounds are soluble polycarboxylic acid esters. The polycarboxylic acid esters have a carbon backbone of from 3 to 12 carbon atoms and 3 or more $C_1$ to $C_5$ alkyl carboxylate groups attached thereto. Suitable polycarboxylic acid esters include for example triethyl citrate, tributyl citrate, triethyl phthalate, tributyl phthalate, tripentyl phthalate or combinations thereof. Preferably, the polycarboxylic acid esters are selected from triethyl citrate, tributyl citrate, tributyl phthalate, or combinations thereof and more preferably are selected from triethyl citrate, tributyl citrate, or combinations thereof.

The second class of compounds are soluble dimethicone copolyols. The name "dimethicone copolyols" is the Cosmetic, Toiletry, and Fragrance Association (CTFA) designation for certain polysiloxane polyether copolymers. The dimethicone copolyols may be represented by the general structure shown in Formula I:

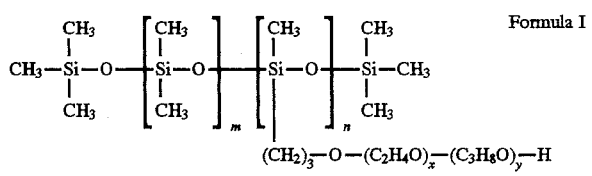

Formula I wherein m, n, x, and y are integers.

The dimethicone copolyols may be linear or branched and may be block or random copolymers. Preferably, the dimethicone copolyols are block copolymers having one or more polysiloxane blocks and one or more polyether blocks.

Preferably, the weight ratio of ethylene oxide ($C_2H_4O$) to propylene oxide ($C_3H_8O$) in the dimethicone copolyols is from 100:0 to 35:65. The viscosity of the dimethicone copolyols as 100 percent actives at 25° C. is preferably from 100 to 4000 centistokes. The dimethicone copolyols are available from suppliers found in the International Cosmetic Ingredients Dictionary, 5th Edition, 1993, published by the CTFA in Washington D.C.

Of the two classes of plasticizing compounds, the soluble polycarboxylic acid esters are preferred.

The plasticizing compounds are preferably added to the hair styling composition to provide a total concentration of from 0.01 to 1.0 weight percent plasticizing compounds, more preferably 0.1 to 0.5 weight percent plasticizing compounds, based on the total weight of the hair styling composition.

The at least one acrylic hair fixative resin which is plasticized by the plasticizing compounds in the low VOC hair styling composition include the hair fixative resins described in U.S. Pat. No. 4,196,190. The acrylic hair fixative resin may be soluble or insoluble in the low VOC hairstyling composition. The acrylic hair fixative resin comprises from 1) 5 to 95, preferably from 45 to 90, and most preferably from 70 to 80 weight percent of at least one $C_1$ to $C_8$ straight or branched chain alkyl (meth)acrylate monomer, 2) from 2 to 70, preferably from 2 to 26, and most preferably from 5 to 20 weight percent of at least one hydroxyalkyl (meth)acrylate monomer, and 3) from 2 to 50, preferably from 2 to 30, and most preferably from 12 to 26 weight percent of at least one $C_3$ to $C_8$ monoethylenically unsaturated monocarboxylic acid monomer, based on the total monomer used to form the acrylic hair fixative resin.

Preferably, the at least one alkyl (meth)acrylate is a $C_1$ to $C_5$ alkyl (meth)acrylate such as for example, methyl (meth)acrylate, ethyl (meth)acrylate, propyl (meth)acrylate, butyl (meth)acrylate, or pentyl (meth)acrylate or combinations thereof.

More preferably the alkyl (meth)acrylate component comprises at least one $C_1$ to $C_3$ alkyl methacrylate and at least one $C_2$ to $C_5$ alkyl acrylate. Most preferably the alkyl (meth)acrylate component comprises methyl methacrylate and butyl acrylate. The weight percent of the at least one $C_1$ to $C_3$ alkyl methacrylate in the hair fixative resin is preferably from 5 to 71, more preferably from 41 to 60 weight percent based on the total monomers used to form the hair fixative resin. The weight percent of the $C_2$ to $C_5$ alkyl acrylate is preferably from 2 to 67 and more preferably from 10 to 30 weight percent, based on the total monomer used to form the acrylic hair fixative resin.

The alkyl group of the hydroxyalkyl (meth)acrylate is preferably a $C_1$ to $C_5$ alkyl group. For example the hydroxyalkyl (meth)acrylate is preferably hydroxymethyl (meth)acrylate, hydroxyethyl (meth)acrylate, hydroxypropyl (meth)acrylate, hydroxybutyl (meth)acrylate, hydroxypentyl (meth)acrylate, or combinations thereof. More preferably the hydroxyalkyl (meth)acrylate is hydroxyethyl methacrylate or hydroxypropyl acrylate or combinations thereof.

The $C_3$ to $C_8$ monoethylenically unsaturated monocarboxylic acid is preferably (meth)acrylic acid, crotonic acid, or combinations thereof. More preferably, the $C_3$ to $C_8$ monoethylenically unsaturated monocarboxylic acid is methacrylic acid.

The proportions of the monomers comprising the acrylic hair fixative resin are selected to provide for an optimum hydrophilic/hydrophobic balance. This optimum balance provides, in a low VOC hair styling composition, curl retention under humid conditions, moisture resistance, shampoo removability, and desirable aesthetics to the hair, such as minimal flaking of the hair fixative resin.

The acrylic hair fixative resin preferably has a weight average molecular weight (Mw) from 40,000 to 100,000, more preferably from 40,000 to 75,000 and most preferably from 40,000 to 60,000, as measured by gel permeation chromatography using a 100,000 Mw methylmethacrylate polymer as the standard. The acrylic hair fixative resin preferably has a calculated glass transition temperatures (Tg) from 40° to 80° C., and most preferably from 45° to 75° C.

The acrylic hair fixative resin is preferably added to the hair styling composition to provide a total concentration of from 1.0 to 15 weight percent and more preferably from 4.0 to 7.0 weight percent hair fixative resin, based on the total weight of the hair styling composition.

The acrylic hair fixative resin may be prepared by conventional methods well known to those skilled in the art. The acrylic hair fixative resin is preferably prepared by emulsion polymerization optionally followed by freeze or spray drying. Preferably, the acrylic hair fixative resin is made by a continuous in-line emulsification process. Suitable emulsion polymerization methods are disclosed in U.S. Pat. Nos. 3,245,932, 3,453,245, and 4,196,190.

In addition to the acrylic hair fixative resin, the low VOC hair styling composition may optionally contain one or more insoluble polyester hair fixative resins. The insoluble polyester hair fixative resins are preferably added to the hair styling composition when the VOC concentration in the hair styling composition is 35 weight percent or less, more preferably 20 weight percent or less, and most preferably 5 weight percent or less, based on the total weight of the hair styling composition. When the concentration of VOC is greater than 35 weight percent, it is preferred that no insoluble resin be present in the hair styling composition.

The insoluble polyester hair fixative resins are preferably added to the hair styling composition to provide a total concentration of from 0 to 10 weight percent; more preferably from 1.0 to 7.0 weight percent; and most preferably from 1.0 to 4.0 weight percent insoluble hair fixative resins, based on the total weight of the hair styling composition. Preferably, the weight ratio of acrylic hair fixative resin to insoluble polyester hair fixative resins in the hair styling composition is from 20:80 to 99:1, more preferably from 40:60 to 80:20.

The insoluble polyester hair fixative resins preferably form hard clear films at room temperature. The insoluble polyester hair fixative resins preferably have a calculated Tg from 30° to 130° C. Preferably, the insoluble polyester hair fixative resins are those described in U.S. Pat. Nos. 3,734,874, 3,779,993, 4,335,220, or 4,233,196. These polyesters can be synthesized by techniques well known to those skilled in the art. Suitable synthesis techniques are disclosed in U.S. Pat. Nos. 3,734,874, 3,779,993, 4,335,220, or 4,233,196.

The preferred insoluble polyester hair fixative resin comprises a reaction product of: at least one difunctional aromatic containing compound, and one or more difunctional compounds selected from dicarboxylic acids, diols, diamines, alcoholamines aminocarboxylic acids, or combinations thereof. The preferred insoluble polyester hair fixative resin also contains one or more metal functional groups selected from a metal sulphonate, a metal carbonate, a nitro group, or combinations thereof.

The difunctional aromatic containing compound contains an aromatic nucleus and two functional groups. The aromatic nucleus may be for example benzene, naphthalene, diphenyl, oxydiphenyl, sulfonyldiphenyl or methylenediphenyl. The two functional groups are each independently selected from a hydroxy, carboxylic acid, or amino group. The two functional groups on the aromatic containing compound must be selected such that they are capable of reacting with the difunctional compounds. The difunctional aromatic containing compound includes for example terephthalic acid, phthalic acid, isophthalic acid, or naphthalene dicarboxylic acid.

The one or more difunctional compounds, as stated previously are selected from dicarboxylic acids, diols, diamines, alcoholamines, aminocarboxylic acids, or combinations thereof.

Dicarboxylic acids which may be used as the difunctional compounds include for example aliphatic or alicylic dicarboxylic acids or combinations thereof. Examples of dicarboxylic acids include succinic, glutaric, adipic, azelaic, sebacic, fumaric, maleic, itaconic, or 1,4-cyclohexanedicarboxylic. Other suitable acids are disclosed in U.S. Pat. No. 3,779,993.

Diols which are suitable as the difunctional compounds include for example aliphatic, alicyclic, and aralkyl glycols. The diols include for example ethylene glycol, propylene glycol, 1,3-propanediol, 2,4-dimethyl-2-ethylhexane-1,3-diol, 2,2-dimethyl-1,3-propanediol; 2-ethyl-2-butyl-1,3-propanediol, 2-ethyl-2-isobutyl-1,3-propanediol, 1,3-butanediol, 1,4-butanediol, 1,5-pentanediol, 1,6-hexanediol, 2,2,4-trimethyl-1,6-hexanediol, thiodiethanol; 1,2-cyclohexanedimethanol, 1,3-cyclohexanedimethanol, 1,4-cyclohexanedimethanol, 2,2,4,4-tetramethyl-1,3-cyclobutanediol, p-xylylenediol, or combinations thereof. The diols may also be polymers such as for example poly(ethylene glycol), or poly(propylene glycol).

Diamines which are suitable as the difunctional compounds include for example ethylenediamine, hexamethylenediamine, 2,2,4-trimethylhexamethylenediamine,4-oxaheptane-1,7-diamine, 4,7-dioxadecane-1,10-diamine, 1,4-cyclohexanebismethylamine, 1,3-cyclohexanebismethylamine, heptamethylenediamine, dodecamethylenediamine, or combinations thereof.

Alcoholamines which are suitable as the difunctional compounds include for example aromatic, aliphatic, heterocyclic compounds containing at least one amino and at least one hydroxy group. Typically, the alcoholamines contain from 2 to 20 carbon atoms. The alcoholamines include for example 5-aminopentanol-1,4-aminomethylcyclohexanemethanol, 5-amino-2-ethylpentanol-1,2-(4-beta-hydroxyethoxyphenyl)-1-aminoethane, 3-amino-2,2-dimethylpropanol, hydroxyethylamine, or combinations thereof.

Aminocarboxylic acids which may be used as the difunctional compounds include aromatic, aliphatic, or heterocyclic compounds containing at least one amino group and at least one carboxylic acid group. Typically the aminocarboxylic acids contain from 2 to 20 carbon atoms. The aminocarboxylic acids include for example 6-aminocaproic acid, its lactam known as caprolactam, omegaaminoundecanoic acid, 3-amino-2-dimethylpropionic acid, 4-(beta-aminoethyl)benzoic acid, 2-(beta-aminopropoxy)benzoic acid, 4-aminomethylcyclohexanecarboxylic acid, 2-(beta-aminopropoxy)cyclohexanecarboxylic acid, or combinations thereof.

The one or more metal functional groups may be attached to the different compounds which comprise the preferred insoluble polyester hair fixative resin. For example, the metal functional groups may be attached to the aromatic nucleus of the difunctional aromatic containing compound, or may be attached to either or both ends of the polyester polymer chain. Preferably the metal functional groups are attached to the aromatic nucleus of the difunctional aromatic containing compound.

The metal of the metal functional group may be for example, an alkali or alkaline earth metal ion, such as sodium, magnesium, calcium, or potassium; or may be for example a transition metal ion such as iron, copper or nickel. The metal functional group is preferably a metal sulfonate group such as sodium sulfonate.

The most preferred insoluble polyester hair fixative resin has the CTFA name "ethylene diglycol/cyclohexanedimethanol/isophthalates/sulphoisophthalates copolymer." This most preferred insoluble hair fixative resin is derived from the reaction of a) at least one difunctional aromatic containing compound having a metal sulfonate group attached to the aromatic nucleus; b) at least one dicarboxylic acid; and c) at least one diol, where at least 20 mole percent of the diol is poly(ethylene glycol). It is commercially available from Eastman Chemical Company.

In a second embodiment of the present invention a low beading, low VOC aqueous hair styling composition is provided. Beads are produced in a sprayed low VOC aqueous hair styling composition when the composition contains at least one soluble surface tension reducing compound and at least one acrylic hair fixative resin. The low beading, low VOC hairstyling composition of the present invention can be obtained by a method comprising adding at least one simethicone to the low VOC hair styling composition containing the soluble surface tension reducing compound and the acrylic hair fixative resin.

An advantage to the simethicone is that it remains stable, and effectively reduces beading in the low beading, low VOC aqueous hair styling composition after extended periods of storage.

Simethicone is the CTFA designation for a mixture containing hydrated silica and dimethylpolysiloxane. The dimethylpolysiloxane has the structure shown in Formula II:

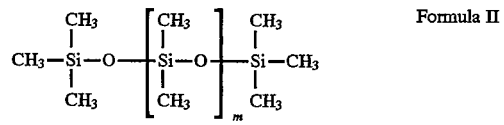

Formula II where m is the average chain length, from 100 to 500.

Simethicone is preferably added to the low beading, low VOC hair styling composition to provide a total concentration of from 0.0001 to 0.5 weight percent simethicone, more preferably from 0.005 to 0.01 weight percent simethicone, based on the total weight of the composition.

Simethicone useful in the present invention may be obtained from suppliers listed in the International Cosmetic Ingredients Dictionary, 5th Edition, 1993, published by the CTFA in Washington D.C. Such suppliers include Dow Corning, Wacker-Chemie, and Rhone Poulenc.

The soluble surface tension reducing compound, as stated previously, is any soluble compound which reduces the surface tension between the hair styling composition and the gaseous atmosphere above the hair styling composition. By "gaseous atmosphere" we mean a propellent or air. The soluble surface tension reducing compound may be for example a plasticizer or surfactant in the hair styling composition. The soluble surface tension reducing compound includes for example dimethiconecopolyols, panthenol, fluorosurfactants, glycerin POE, PPG 28 Buteth 35, PEG 75 lanolin, octoxynol-9, PEG-25 hydrogenated castor oil, polyethylene glycol 25 glyceryl trioleate, oleth-3 phosphate, PPG-5-ceteth-10 phosphate, PEG-20 methyl glucose ether, or glycereth-7-triacetate, glycereth-7-benzoate or combinations thereof. Preferably the soluble surface tension compound is dimethiconecopolyols, panthenol, glycereth-7-benzoate, or combinations thereof.

The soluble surface tension reducing compound is typically present in the low beading, low VOC hairstyling composition at a concentration of from 0.01 to 1 weight percent, and more preferably at a concentration of from 0.01 to 0.25 weight percent, based on the total weight of the composition.

The acrylic hair fixative resin, described previously herein, is preferably added to the low beading, low VOC hair styling composition to provide a total concentration of from 1.0 to 15 weight percent, and more preferably from 3.0 to 7.0 weight percent, based on the total weight of the hair styling composition.

In addition to the acrylic hair fixative resin, one or more of the insoluble polyester hair fixative resins, described previously herein, may optionally be present in the low beading, low VOC hair styling composition. The insoluble polyester hair fixative resins are preferably added to provide a total concentration of from 0 to 10 weight percent; more preferably from 1.0 to 7.0 weight percent; and most preferably from 1.0 to 4.0 weight percent insoluble polyester hair fixative resins, based on the total weight of the hair styling composition. Preferably the weight ratio of acrylic hair fixative resin to insoluble polyester hair fixative resins in the low beading, low VOC hair styling composition is from 20:80 to 99:1, and more preferably from 40:60 to 80:20.

In a third embodiment of the present invention, an aqueous hair resin composition containing iodopropynylbutyl carbamate and at least one acrylic hair fixative resin is provided. Iodopropynylbutyl carbamate when added to the aqueous hair resin composition provides a method of inhibiting microbial growth in the aqueous hair resin composition. Iodopropynlbutyl carbamate is commercially available from Lonza.

Iodopropynylbutylcarbamate is effective in preventing microbial growth such as fungus or mold in the aqueous hair resin composition. Iodopropynylbutyl carbamate is particularly suitable as a preservative in the aqueous hair resin composition having a pH of less than 4.5. The iodopropynylbutylcarbamate is compatible in the acrylic hair resin emulsion and in the hair styling composition.

Preferably, Iodopropynylbutylcarbamate is added to the aqueous hair resin composition to provide a concentration of from 0.001 to 1 weight percent iodopropynyl butyl carbamate based on the total weight of the aqueous hair resin composition.

The aqueous hair resin composition preferably contains a concentration of from 1 to 60 weight percent, more preferably from 5 to 44 weight percent of the acrylic hair fixative resin previously described herein, based on the total weight of the aqueous hair resin composition. The aqueous hair resin composition may be the composition that the acrylic hair fixative resin is dissolved or suspended in before being added to the hair styling composition, hereinafter called the "acrylic hair resin emulsion." The aqueous hair resin composition may also be the aqueous hair styling composition.

The acrylic hair resin emulsion is preferably an aqueous emulsion which was obtained from the process which produced the acrylic hair fixative resin. The acrylic hair resin emulsion typically has apH from 2.0 to 4.5. The acrylic hair resin emulsion preferably contains from 30 to 60 weight percent of the acrylic hair fixative resin, from 30 to 70 weight percent water, from 0.01 to 1.0 weight percent of one or more emulsifiers, and from 0.005 to 0.05 weight percent of the iodopropynylbutylcarbamate, based on the total weight of the acrylic hair resin emulsion.

The one or more emulsifiers keeps the acrylic hair fixative resin suspended in the acrylic hair resin emulsion. Typical emulsifiers include for example sodium lauryl sulfate, sodium tridecylether sulfate, diester sulfosuccinates, alkyl or aryl polyether sulfonates, alkyl or aryl polyether alcohols, or ethylene oxide condensates of propylene oxide, propylene glycol adducts or combinations thereof.

The aqueous hair styling composition may be for example, the low VOC aqueous hair styling composition or the low beading, low VOC hairstyling composition described previously herein. Iodopropynylbutyl carbamate is preferably present in the aqueous hair styling composition when the aqueous hair styling composition contains greater than 60 weight percent water. The iodopropynyl butylcarbamate is preferably added to the aqueous hair styling composition to provide a total concentration of from 0.005 to 0.02 weight percent iodopropynyl butylcarbamate, based on the total weight of the hair styling composition. Other preservatives may also be added to the hair styling composition.

The first, second, and third embodiments may also contain other hair fixative resins, neutralizers, surfactants, solvents, propellants, other preservatives, thickeners, and other additives.

Other hair fixative resins may optionally be added to the aqueous hair styling composition to provide other properties which may be desired by the formulator, such as a "stiffer" hold of the hair. The other hair fixative resins may be soluble or insoluble in the aqueous hair styling composition. The other hair fixative resins may be present in the aqueous hair styling composition at a concentration of from 0.5 to 6.0 weight percent, preferably from 1.0 to 2.0 weight percent, based on the total weight of the hair styling composition.

The other hair fixative resins which are suitable in the aqueous hair styling composition include for example butyl acrylate/ethyl acrylate/methacrylic acid copolymers; vinyl pyrrolidone/vinyl acetate compolymers; octylacrylamide/acrylates/butyl-aminoethylmethacrylate copolymers; vinylcaprolactam/vinylpyrrolidone/dimethylaminoethylmethlacrylate copolymers; methacryloyl ethyl-betaine/methacrylate copolymers; methacrylic acid/methacrylic ester copolymer; or methacrylic acid/acrylic acid ester copolymers; or combinations thereof.

Neutralizers are preferably present in the hairstyling composition when the hair fixative resins contain acidic groups, such as carboxylic acid groups, to promote solubility of the resin in the aqueous hair styling composition. For example, the acrylic hair fixative resin is preferably partially neutralized.

Bases which will neutralize the hair fixative resins include for example amines, alkali or alkaline earth metal hydroxides, ammonium hydroxide or combinations thereof. Suitable amine neutralizers include for example 2-amino-2-methyl propanediol, 2-amino 2-methyl propanol, N,N dimethyl 2-amino 2-methyl 1-propanol, monoisopropanolamine, triisopropanolamine, ethanolamine, triethanolamine, morpholine or combinations thereof. Suitable alkali or alkaline earth metal hydroxides include for example sodium hydroxide potassium hydroxide, or combinations thereof. Preferably, the neutralizer is selected from the group consisting of 2-amino 2-methyl propanediol, 2-amino-2-methyl propanol, N,N dimethyl 2-amino 2-methyl propanol, potassium hydroxide, triethanolamine, triisopropanolamine, or combinations thereof.

The amount of neutralizer added to the aqueous hair styling composition is preferably that amount to provide solubility of the hair fixative resin in the hair styling composition. Preferably, in a hair styling composition containing 35 weight percent or less VOC, from 40 to 60 mole percent of the acid groups on the hair fixative resin are neutralized. For a VOC hair styling composition containing greater than 35 weight percent VOC, preferably greater than 60 mole percent of the acid groups on the hair fixative resin are neutralized.

One or more surfactants may be added to the aqueous hair styling composition. When surfactants are present in the hair styling composition, they are preferably present at a concentration of from 0.001 to 1.0 weight percent, based on the total weight of the composition. The surfactants which may be used in the hair styling composition include for example anionic, cationic, nonionic, or amphoteric surfactants. For example, suitable surfactants include PPG 28 Buteth 35, PEG 75 lanolin, perfluoropolymethyl isopropyl ether, octoxynol-9, PEG-25 hydrogenated castor oil, polyethylene terephthalate, polyethylene glycol 25 glceryl triloeate, oleth-3-phosphate, PPG-5-ceteth-10 phosphate, PEG-20 methyl glucose ether, glycereth-7-triacetate, glycereth-7-benzoate, or n-alkyl substituted lactam such as n-octyl pyrrolidone, or combinations thereof.

One or more solvents may be added to the aqueous hair styling composition of the present invention. The solvents may or may not be VOC. When solvents are added to the aqueous hair styling composition they preferably comprise 70 weight percent or less, and more preferably 55 weight percent or less, based on the total weight of the aqueous hair styling composition. Suitable solvents include for example $C_1$ to $C_{12}$ straight or branched chain alcohols such as methanol, ethanol, isopropanol, or propanol or combinations thereof.

In an aqueous hair styling composition using an aerosol spray, one or more propellants are used. The propellants may or may not be VOC. Preferably, the propellants are used at a total concentration of from 10 to 70 weight percent; and more preferably from 30 to 60 weight percent, based on the total weight of the aqueous hair styling composition. Propellants include for example n-butane, isobutane, dimethyl ether; dimethoxymethane, difluoroethane, chlorodifluoroethane, chlorodifluoromethane, other chlorofluorocarbons, or combinations thereof. Preferred propellants are dimethyl ether, 1,1-difluoroethane, n-butane, isobutane, or combinations thereof. These propellants are commercially available.

As stated previously, the total VOC in the aqueous hair styling composition, whether the VOC is a solvent or propellant, should be 70 weight percent or less, based on the total weight of the aqueous hair styling composition.

Other preservatives which may be used in the aqueous hair styling composition include for example isothiazolones, benzyl alcohol, or imidazolidinylurea. The other preservatives preferably comprise from 0.001 to 1.0 weight percent of the hair styling composition.

One or more thickeners may be desirable in a hair styling composition which is applied to the hair in the form of a mousse or styling gel. Suitable thickeners include for example polycarboxylic acid thickeners such as acrylates/steareth-20 methacrylate copolymer, carbomers, acrylates copolymer, or acrylates $C_{10-30}$ alkyl acrylate crosspolymer; polyethoxylated urethane thickeners, or polyamide thickeners. The thickeners, when used, preferably are present at a total concentration of from 0.001 to 5.0 weight percent based on the total weight of the composition.

Other additives, such as those commonly used by those skilled in the art may be added to the hair styling composition. The other additives used in the hair styling composition will depend upon the type of hair styling composition desired. Other additives include for example fragrances; moisturizers such as hydrolyzed silk protein, or hydrolyzed wheat protein; detangling aids such as panthenol; conditioning agents, such as those disclosed in U.S. Pat. No. 5,164,177; emulsifiers; antistatic aids, extracts, proteins, vitamins, dyes, tints, colorants, UV protectors or combinations thereof. The other additives typically comprise from 0.005 to 5 weight percent; more preferably from 0.01 to 1 weight percent of the aqueous hair styling composition, based on total weight of the aqueous hair styling composition.

Additional other additives, as well as additional surfactants, solvents, other preservatives, and thickeners, which may be suitable in the aqueous hair styling composition may be found in the International Cosmetic Ingredients Dictionary, 5th Edition, 1993, published by the CTFA in Washington D.C.

Some embodiments of the invention will now be described in detail in the following Examples. In all examples, unless otherwise stated, the acrylic hair fixative resin tested, herein after referred to as "Hair Resin 1", had a weight average molecular weight of 50,000 and consisted of the following components in Table 1:

Table 1: Composition of Hair Resin 1
  25 weight percent butyl acrylate
  47 weight percent methyl methacrylate
  10 weight percent hydroxyethylmethacrylate
  18 weight percent methacrylic acid The weight average molecular weight of the acrylic hair fixative resins was measured by gel permeation chromatography using a 100,000 Mw methylmethacrylate polymer as a standard.

Hair Resin 1 was added to the aqueous hair styling compositions in Examples 1 to 27 as an aqueous emulsion having 41 weight percent active solids and having a pH of about 2.5. All concentrations of Hair Resin 1 added to the hair styling compositions are reported as active solids.

The Hair Resin 1 was made similar to the procedure described in Example 1 of U.S. Pat. No. 4,196,190 except that n-dodecyl mercaptan was used as the chain regulator instead of bromotrichloroethane.

In Examples 1 to 29, test hair styling compositions having 55 weight percent VOC were prepared and consisted of the following components shown in Table 2.

TABLE 2

55 Weight Percent VOC Test Hair Styling Compositions for Examples 1 to 29

| Test Composition Name | Test Hair Styling Composition (weight percent) | | | |
|---|---|---|---|---|
| Components | C1 | A | B | D |
| Hair Resin 1 (as active solids) | 5.1 | 5.1 | 5.1 | 3.5 |
| Hair Resin 3 | — | — | — | 1.5 |
| 2-amino-2-methylpropanol | 0.56 | 0.56 | 0.56 | 0.65 |
| Ethanol | 55.0 | 55.0 | 55.0 | 55.0 |
| Plasticizing compound tested | — | see Table 6 | — | see Table 10 |
| Surface Tension Reducing compound | — | — | see Table 8 | — |
| Simethicone | — | — | see Table 8 | — |
| Water | Balance | Balance | Balance | Balance |

In Examples 1 to 8, the plasticizing compounds useful in the present invention were evaluated for their ability to plasticize the acrylic hair fixative resins. The plasticizing compounds, useful in the present invention, in Examples 1 to 8 were also evaluated for performance in low VOC hair styling compositions in Examples 1 to 8. The plasticizing compounds were evaluated by preparing test hair styling compositions according to the test hair styling composition A, which contained the one or more plasticizing compounds. Each test hair styling composition was then applied to hair to evaluate the following properties: comb-through, feel, percent curl retention, drying time, and tackiness. The performance of the test hair styling composition was compared to the performance of the C1 hair styling composition, which contained no plasticizing compound.

The comb-through and feel properties are an indication of the plasticizing compound's effectiveness in plasticizing the hair fixative resin. The plasticizing compound should increase the ease of combing and decrease breakage of the film upon combing in comparison to a control having no plasticizing compound. The plasticizing compound should also impart softness to the hair in comparison to the control.

Additionally, the plasticizing compound should not significantly decrease the percent curl retention, increase the drying time, and increase the tackiness of the test hair styling composition in comparison to the C1 hair styling composition (having no plasticking compound).

The following procedure was used to evaluate each test hair styling composition:

Each test hair styling composition was sprayed on a 3 gram swatch of European brown virgin hair having a length of 7 inches (17.78 cms) and supplied by DeMeo Brothers located in Brooklyn, N.Y. The hair swatch was prepared by cementing together at the root end the European brown virgin hair. Each hair swatch was then washed with a dilute solution of Suave® shampoo (registered trademark of Helene Curtis), followed by rinsing with ambient deionized water.

Each test hair styling composition was sprayed onto the hair swatch using a Euromist II spray valve having dimensions of 0.014 inches by 0.010 inches deep (in metric units, 0.0356 cm by 0.0254 cm deep) supplied by Seaquist Dispensing located in Cary, Ill. The spray valve dispensed about 140 microliters per pump stroke.

For evaluating drying time, tack, comb-through, and feel, approximately 700 microliters of the test hair styling composition was sprayed on the hair swatch and the hair swatch was allowed to dry hanging vertically.

The hair swatch was felt by hand for tackiness (or stickiness) and evaluated using the following scale in Table 3:

Table 3: Tackiness Scale
1=Very low or no tack on the hair after about 60 seconds
2=Slight tack after about 60 seconds
3=Severe tackiness or stickiness during drying, or after 60 seconds
4=Stickiness during or after drying which leads to matting or netting of hair After the hair swatch was dry to the touch, the drying time was recorded. Next, the hair swatch was combed through several times to evaluate the ease of combing and to evaluate the breakage or cracking of the hair resin film from combing. The following comb-through scale was used as shown in Table 4.

Table 4: Comb-through Scale
1=Easy to comb through, no or virtually no visible residue on the comb or hair after combing.
2=Easy to comb through, but slight visible residue on the comb or hair after combing.
3=Slight raspy feel during combing, needing a little force to comb, slight visible residue on the comb or hair after combing.
4=Severe raspy feeling during combing needing force and visible residue on hair or comb after combing.

The dried hair swatch was also felt by hand and evaluated for feel according to the following scale shown in Table 5:

Table 5: Feel Scale
1=Softer feel on the hair than control
2=Soft feel on hair, value assigned to control
3=Slight harsh feel on the hair (meaning stiffer)

Percent curl retention of each test hair styling composition was evaluated by rolling the hair swatch, previously described, in a curler having a diameter of about 3 cms. The hair was then sprayed with about 700 microliters of the test hair styling composition. The hair was allowed to dry for about 30 minutes. After drying, the curler was removed from the hair and the hair was placed in a chamber having 95 percent relative humidity for 8 hours. The percent curl retention was measured by measuring the length of the hair initially after curling ($L_i$), the length of the hair after exposure to humidity ($L_r$), and the length of the hair fully extended, before curling ($L_e$). The following equation (Formula III) was used to calculate percent curl retention.

$$\% \text{ Curl Retention} = \frac{(L_i - L_r) \times 100}{(L_i - L_e)} \quad \text{Formula III}$$

The results of evaluating the plasticizing compounds useful in the present invention in the hair styling composition A are shown in Table 6. The results in Table 6 show that the dimethiconecopolyols and the polycarboxylic acid esters improve comb-through and feel of the acrylic hair fixative resin without significantly affecting drying time, curl retention, or tackiness. The dimethicone copolyols (Examples 6 to 7) and the triethylcitrate (Example 8) improved the comb-through and feel of the hair styling composition in comparison to C1 (Comparative Example 1), having no plasticizing compound. Comparative Examples 2 and 3, although improving the comb-through and feel of the hair styling composition, adversely affect curl retention, drying time, or tackiness in comparison to C1 (Comparative Example 1). Comparative Examples 4 and 5 do not provide any improvement in comb through or feel in the test hair styling composition A in comparison to C1.

TABLE 6

Effectiveness of Plasticizing Compounds in Low VOC Hair Styling Compositions

| Example | HS[1] | Plasticizing Compound[2] | Plast. Conc.[3] (wt %) | % CR[4] | Dry Time[5] (sec) | Tack[6] | Comb[7] | Feel[8] |
|---|---|---|---|---|---|---|---|---|
| 1 (comp)* | C1 | none | 0.0 | 87 | 48 | 1.0 | 2.0 | 2.0 |
| 2 (comp) | A | PEG 500 | 0.1 | 74 | 55 | 2.0 | 1.2 | 1.4 |
| 3 (comp) | A | glycerin POE | 0.1 | 84 | 54 | 2.0 | 1.4 | 1.6 |
| 4 (comp) | A | dimethicone | 0.1 | — | — | 1.0 | 2.0 | 2.0 |
| 5 (comp) | A | cyclomethicone | 0.1 | — | — | 1.5 | 2.0 | 2.0 |
| 6 | A | dimethiconecopolyol 1 | 0.1 | 88 | 51 | 1.0 | 1.5 | 1.0 |
| 7 | A | dimethiconecopolyol 2 | 0.1 | 86 | 52 | 1.0 | 1.5 | 1.0 |
| 8 | A | triethylcitrate | 0.2 | 85 | 49 | 1.2 | 1.6 | 1.6 |

[1]Test hair styling composition described in Table 2.
[2]Plasticizing compounds are described in Table 14
[3]Concentration of plasticizing compound in the test hair styling composition A in weight percent.
[4]Percent Curl Retention.
[5]Drying time, in seconds, of the test hair styling composition after being sprayed on the hair swatch.
[6]Tackiness according to the scale in Table 3.
[7]Comb-through according to the scale in Table 4.
[8]Feel according to the scale in Table 5.
*comparative The effectiveness of the simethicone in reducing beading on hair from a sprayed low VOC hair styling composition containing at least one soluble surface tension reducing compound and at least one hair fixative resin was evaluated.

The procedure for evaluating beading in low VOC hair styling compositions was the same as that used for evaluating the performance of the plasticizing compounds in low VOC hair styling compositions, except that after the hair styling composition was sprayed on the hair swatch, the hair swatch was visually ranked for beading using the scale shown in Table 7:

Table 7: Beading Scale
1=no beading on the hair after drying or after spraying.
2=slight beading after spraying, but no beading after drying.
3=slight beading, slight residue from beads after drying.
4=severe beading, noticeable residue after drying.

The hair styling compositions were also evaluated for tackiness, comb-through, and feel according to the procedure previously described.

The results of evaluating the simethicone for reducing beading in 55 weight percent VOC hair styling compositions are shown in Table 8. The results in Table 8 show that by adding simethicone (Examples 13 to 16) to a low VOC hair styling composition containing a surface tension reducing compound, such as dimethiconecopolyol, beading on the hair is reduced in comparison to a low VOC hairspray composition containing the surface tension reducing compound but no simethicone (Comparative Examples 11 to 12). Examples 13 to 16 also demonstrate that the addition of the simethicone does not adversely affect tackiness, comb-through, or feel. Comparative Example 10 demonstrates that triethylcitrate, in addition to plasticizing the hair fixative resin, also reduces the beading in low VOC hair styling compositions.

TABLE 8

Effectiveness of Simethicone in Reducing Beading in Low VOC Hair Styling Compositions

| Example | HS | Surface Tension Reducing Compound | S Conc.[9] (pbw) | SMC Conc.[10] (pbw) | Bead[11] | Tack | Comb | Feel |
|---|---|---|---|---|---|---|---|---|
| 9 (comp) | C1 | none | 0.0 | 0.0 | 2.0 | 1.0 | 2.0 | 2.0 |
| 10 (comp) | A | triethylcitrate* | 0.2 | 0.0 | 1.4 | 1.2 | 1.6 | 1.6 |
| 11 (comp) | B | dimethiconepolyol 1 | 0.1 | 0.0 | 2.5 | 1.0 | 1.5 | 1.0 |
| 12 (comp) | B | dimethiconepolyol 2 | 0.1 | 0.0 | 2.5 | 1.0 | 1.5 | 1.0 |
| 13 | B | dimethiconepolyol 1 | 0.1 | 0.01 | 1.4 | 1.0 | 1.5 | 1.0 |
| 14 | B | dimethiconepolyol 1 | 0.2 | 0.01 | 1.6 | 1.2 | 1.2 | 1.0 |
| 15 | B | dimethiconepolyol 3 | 0.1 | 0.01 | 1.4 | 1.0 | 1.5 | 1.5 |
| 16 | B** | glycereth-7-benzoate | 0.1 | 0.01 | 1.2 | 1.2 | 1.2 | 2.0 |

[9]Concentration of plasticizing compound or surface tension reducing compound in parts by weight
[10]Concentration of simethicone in parts by weight.
[11]Beading measured according to the scale in Table 7.
*A plasticizing compound.
**Example 16 also contained 0.1 weight percent triethyl citrate.

The acrylic hair fixative resins useful in the present invention were evaluated for the effect of resin weight average molecular weight (Mw) on the performance of low VOC hair styling compositions.

The following procedure was used to evaluate the performance of low VOC hair styling compositions containing an acrylic hair fixative resin having a Mw ranging from 40,000 to 150,000. Low VOC hair styling compositions were prepared according to the test hair styling composition C1 in Table 2, except that Hair Resin 1 had a Mw as shown in Table 9. The performance of the low VOC hair styling compositions prepared were evaluated for percent curl retention, beading, drying time, tackiness, and feel, according to the procedures described previously. The viscosities of the low VOC hair styling compositions were also measured at a temperature of 22° C. using a Brookfield viscometer using spindle #1, at 60 rpm.

The results of evaluating the performance of the low VOC hair styling compositions containing the acrylic hair fixative resin ranging in Mw from 40,000 to 150,000 are shown in Table 9. Examples 17 and 18 indicate that an acrylic hair fixative resin having the composition of Hair Resin 1, but having a Mw greater than or equal to 100,000 contributed to increased beading, drying time, tackiness, and formulation viscosity in comparison to Hair Resin 1 (Example 20) in a sprayed low VOC hair styling composition.

The viscosity of the low VOC hair styling composition in Example 18 was lowered to a viscosity of 9.8 centipoise by the addition of a monovalent electrolyte metal salt (0.5 parts by weight sodium chloride). The addition of the sodium chloride decreased the beading to a value of 2 in comparison to Example 18. However the monovalent electrolyte metal salt decreased the shine or gloss of the hair and contributed to a raspy feel of the hair when combing.

The results in Table 9 (Examples 17 to 21) also show that the percent curl retention improves as the molecular weight is increased.

The acrylic hair fixative resin was formulated with another hair fixative resin according to Test Hair Styling Composition D shown in Table 2 to provide a "stiffer" hold. Test Hair Styling Composition D was evaluated for percent curl retention, tackiness, comb-through, feel, drying time, and beading using the test methods previously described. The results are shown in Table 10.

Example 22 shows that another hair fixative resin can be added to provide a stiffer hold. For example, Example 22 had a greater value for "Feel" in comparison to Comparative Example 1, shown in Table 6, having no hair resin 3. (A stiffer hold is indicated by a greater measured value for "Feel.")

TABLE 10

| | Combination of Acrylic Hair Fixative Resin with Other Hair Fixative Resin | | | | | | |
|---|---|---|---|---|---|---|---|
| Example | Plasticizer | % CR | Bead | Dry Time (sec) | Comb | Tack | Feel |
| 22 | 0.2 wt % triethyl citrate and 0.1 wt % dimethiconecopolyol 1 | 86 | 2.0 | 51 | 1.6 | 1.4 | 2.6 |

The iodopropynylbutylcarbamate useful in the present invention was evaluated for its effectiveness in inhibiting microbial growth in aqueous hair resin compositions.

The following procedure was used for evaluating the iodopropynylbutylcarbamate. The iodopropynylbutylcarbamate was added at several concentrations to an aqueous hair resin emulsion containing Hair Resin 1. The aqueous hair resin emulsion contained 41 weight percent active solids of Hair Resin 1, 0.20 weight percent sodium lauryl sulfate as an emulsifier, and water. The acrylic hair resin emulsion had a pH of 2.5. Ten grams of each aqueous hair resin emulsion, containing the iodopropynylbutylcarbamate, was then inoculated with a mixture of yeast, fungi, and bacteria. The inoculated aqueous hair resin emulsions were stored at a temperature of either 25° C. or 45° C. for a week. At the end of the week, 0.1 grams of each inoculated aqueous hair resin emulsion was streaked on trypticase soy agar. The streak plates were incubated at 30° C. for 5 days. At the end of five days the streak plates were evaluated for microbial growth using the following scale in Table 11:

TABLE 9

Effect of Acrylic Hair Fixative Resin Mw on Performance of Sprayed Low VOC Hair Styling Composition

| Example | HS | Mw of Hair Resin[12] | Visc.[13] (cps) | % CR | Bead | Dry Time (sec) | Tack | Feel |
|---|---|---|---|---|---|---|---|---|
| 17 | C1 | 150,000 | 24.1 | 92 | — | — | — | — |
| 18 | C1 | 100,000 | 18.6 | 92 | 3.0 | 58 | 2.5 | 2.6 |
| 19 | C1 | 60,000 | 9.5 | 88 | — | — | — | — |
| 20 | C1 | 50,000 | 8.8 | 87 | 2.0 | 48 | 1.0 | 2.0 |
| 21 | C1 | 40,000 | 8.5 | 88 | — | — | — | — |

[12]Weight average molecular weight of the hair fixative resin.
[13]Viscosity of hair styling composition measured in centipoise.

TABLE 11

| Microbial Growth Scale | |
|---|---|
| Streak Plate Rating | Growth |
| 0 | no growth |
| T | trace |
| 1 | very light growth |
| 2 | light growth |

TABLE 11-continued

| Microbial Growth Scale | |
|---|---|
| Streak Plate Rating | Growth |
| 3 | moderate growth |
| 4 | heavy growth |

The inoculated aqueous emulsion was reinoculated and streaked once every week for three weeks. Other preservatives, as comparatives, were evaluated for their ability to prevent of microbial growth by the same procedure used to evaluate the iodopropynylbutylcarbamate. The results of the iodopropynylbutylcarbamate to prevent microbial growth in the aqueous hair resin composition is shown in Table 12.

The iodopropynylbutylcarbamate and other preservatives (as comparatives) were evaluated for stability in the aqueous hair resin emulsion. Each aqueous hair resin emulsion containing a preservative was stored at 45° C. for one week. If after one week the aqueous hair resin emulsion changed color or phase separated, the preservative was designated as "fail" in Table 12. If the preservative did not change color or phase separate, the preservative was designated in Table 12 as being "ok."

The aqueous hair resin emulsion containing the iodopropynylbutylcarbamate or other preservatives were formulated into low VOC hair styling compositions according to the test hair styling composition C1. The hair styling composition containing the preservative was then evaluated for comb-through and feel according to the procedure described previously. If the hair styling composition containing the preservative had worse comb-through and feel compared to Comparative Example 1, the preservative was designated in Table 12 as "neg", having negative performance effects. If the performance of the hair styling composition containing the preservative had the same or better performance in comparison to Comparative Example 1, the preservative was designated in Table 12 as having "ok" performance.

The results of evaluating the preservatives in aqueous hair resin compositions are shown in Table 12. Table 12 (Examples 26 to 29) demonstrates that iodopropynlbutylcarbamate is effective in inhibiting microbial growth and does not destabilize the acrylic hair resin emulsion. Iodopropynlbutylcarbamate also does not hurt the performance of the aqueous hair styling composition.

TABLE 12

Effectiveness of Preservatives in Aqueous Hair Resin Compositions

| Example | Preservative[16] | Pres. Conc.[17] (wt %) | T[18] (°C.) | Growth Rate[19] | | | Emul. Stab.[20] | Perf.[21] |
|---|---|---|---|---|---|---|---|---|
| | | | | 1st inoc | 2nd inoc | 3rd inoc | | |
| | none | 0.0 | — | 4 | 4 | — | ok | ok |
| 23 (comp) | potassium sorbate | 0.5 | 45 | 0 | 0 | 0 | fail | neg |
| 24 (comp) | methyl parben | 0.5 | 25 | 4 | 4 | — | ok | ok |
| 25 (comp) | sodium benzoate | 0.5 | 25 | 3 | 4 | — | — | — |
| 26 | IPBC | 0.03 | 25 | 0 | 0 | 0 | ok | ok |
| 27 | IPBC | 0.03 | 45 | 0 | 0 | 0 | ok | ok |
| 28 | IPBC | 0.01 | 25 | 0 | 0 | 0 | ok | ok |
| 29 | IPBC | 0.005 | 25 | T | 1 | 1 | ok | ok |

[16]Preservative IPBC is described in Taable 14.
[17]Preservative concentration in the hair styling composition in weight percent.
[18]Temperature microbial growth test performed at in °C.
[19]Growth rate of microbes measured after 5 days from each inoculation.
[20]Emulsion stability.
[21]Performance of preservative in test hair styling composition C1.

Low VOC hair styling compositions were prepared according to the compositions in Table 13. Examples of suitable hair spray compositions which can be used with a spray pump (compositions D, E, H) and aerosol spray (compositions F and G) are shown in Table 13. Composition D is an example of a 0 weight percent VOC hair styling composition containing an acrylic hair fixative resin and insoluble polyester hair fixative resin. Composition I is an example of a styling gel formulation which is applied to hair by hand.

TABLE 13

Low VOC Hair Styling Compositions

| Components | Low VOC Hair Styling Composition (weight percent) | | | | | |
|---|---|---|---|---|---|---|
| Composition Name | D | E | F | G | H | I |
| Type | pump | pump | aerosol | aerosol | pump | gel |
| VOC Content (wt %) | 0 | 55 | 55 | 55 | 70 | 6 |
| Hair Resin 1 | 3.1 | 7.0 | 5.1 | 5.1 | 7.0 | 4.0 |
| Hair Resin 2* | 3.2 | — | — | — | — | — |
| 2-amino-2-methylpropanol | 0.42 | 0.76 | 0.56 | 0.56 | 0.76 | 0.62 |
| ethanol | 0.0 | 55.0 | 25.0 | 55.0 | 70.0 | 6.0 |
| triethyl citrate | 0.1 | — | — | — | — | 0.10 |
| dimethiconecopolyol 1* | — | 0.1 | 0.1 | 0.1 | — | — |
| simethicone* | — | — | — | — | — | — |
| dimethylether | — | — | 30.0 | — | — | — |
| HFC-152a* | — | — | — | 30.0 | — | — |
| thickener* | — | — | — | — | — | 3.2 |
| Water | Balance | Balance | Balance | Balance | Balance | Balance |

*Component is described in Table 14.

TABLE 14

Description of Components used in Hair Styling Compositions in Example 1–29 and Table 13

| Component | Description |
|---|---|
| dimethiconecopolyol 1 | Dow Corning ® 190 Surfactant, registered trademark of Dow Corning |
| dimethiconecopolyol 2 | Dow Corning 193 Surfactant |
| dimethiconecopolyol 3 | Dow Corning Q2-5220 |
| simethicone | Dow Corning Antifoam A |
| cyclomethicone | Dow Corning 344 Fluid |
| dimethicone | Dow Corning 200 Fluid |
| IPBC | iodopropynylbutylcarbamate |
| Hair Resin 2 | Eastman AQ-55 Resin, supplied by Eastman Kodak (ethylenediglycol/cyclohexanedimethanol/isophthalates/sulphoisophthalates copolymer) |
| Hair Resin 3 | Octylacrylamide/Acrylates/Butylaminoethyl Methacrylate Copolymer |
| PEG 500 | poly(ethylene glycol) having a molecular weight of 500 |
| Glycerin POE | Polyethoxylated glycerin, supplied by Calgine Chemical |
| HFC-152a | 1,1-difluoroethane or Dymel ® 152a, registered trademark of DuPont |
| Thickener | Acrylates/Steareth-20 methacrylate copolymer |

I claim:

1. An aqueous hair styling composition, comprising:

A) from 1 to 15 weight percent of at least one acrylic hair fixative resin wherein the acrylic hair fixative resin comprises from 1) 5 to 95 weight percent of at least one $C_1$ to $C_8$ straight or branched chain alkyl (meth)acrylate monomer, 2) from 2 to 70 weight percent of at least one hydroxyalkyl (meth)acrylate monomer, and 3) from 2 to 50 weight percent of at least one $C_3$ to $C_8$ monoethylenically unsaturated monocarboxylic acid monomer, based on the total weight of monomer;

B) from 0 to 10 weight percent of one or more insoluble polyester hair fixative resins;

C) from 0.01 to 1.0 weight percent of one or more soluble plasticizing compounds selected from the group consisting of polycarboxylic acid esters and dimethicone copolyols, wherein the polycarboxylic acid esters comprise a carbon backbone containing 3 to 12 carbon atoms and at least three $C_1$–$C_5$ alkyl carboxylate groups attached thereto;

D) from 15 to 98 weight percent water; and

E) 70 weight percent or less of one or more volatile organic compounds.

2. The aqueous hair styling composition of claim 1, wherein: the acrylic hair fixative resin comprises from 5 to 71 weight percent of at least one $C_1$ to $C_3$ alkyl methacrylate monomer; from 2 to 67 weight percent of at least one $C_2$ to $C_5$ alkyl acrylate monomer; from 2 to 26 weight percent of at least one hydroxyalkyl (meth)acrylate monomer; and from 2 to 30 weight percent of at least one $C_3$ to $C_8$ monoethylenically unsaturated monocarboxylic acid monomer, based on the total weight of monomer.

3. The aqueous hair styling composition of claim 1, wherein: the insoluble polyester hair fixative resins comprise a reaction product of: at least one difunctional aromatic containing compound, and one or more difunctional compounds selected from the group consisting of dicarboxylic acids, diols, diamines, alcoholamines aminocarboxylic acids, and combinations thereof.

4. The aqueous hair styling composition of claim 1, wherein: the insoluble polyester hair fixative resins are ethylenediglycol/cyclohexanedimethanol/isophthalates/sulphoisophthalates copolymers.

5. The aqueous hair styling composition of claim 1, wherein: the plasticizing compounds are selected from the group consisting of: triethyl citrate, tributyl citrate, triethyl phthalate, tributyl phthalate, tripentyl phthalate and combinations thereof.

6. The aqueous hair styling composition of claim 1, wherein: the plasticizing compounds are dimethiconecopolyols.

7. The aqueous hair styling composition of claim 1, wherein the concentration of the volatile organic compounds is 55 weight percent or less.

8. The aqueous hair styling composition of claim 1, further comprising: at least one propellant.

9. A method of plasticizing an acrylic hair fixative resin in an aqueous hair styling composition, comprising: adding to the hair styling composition one or more soluble plasticizing compounds selected from the group consisting of: polycarboxylic acid esters and dimethicone copolyols wherein the polycarboxylic acid esters comprise a carbon backbone containing 3 to 12 carbon atoms and at least three $C_1$–$C_5$ alkyl groups attached thereto;

wherein the acrylic hair fixative resin comprises from 1) 5 to 95 weight percent of at least one $C_1$ to $C_8$ alkyl (meth)acrylate monomer, 2) from 2 to 70 weight percent of at least one hydroxyalkyl (meth)acrylate monomer, and 3) from 2 to 50 weight percent of at least one $C_3$ to $C_8$ monoethylenically unsaturated monocarboxylic acid monomer, based on the total weight of monomer; and wherein the aqueous hair styling composition contains from 15 to 98 weight percent water and 70 weight percent or less of one or more volatile organic compounds.

10. A low beading aqueous hair styling composition, comprising:

A) from 1 to 15 weight percent of at least one acrylic hair fixative resin;

B) from 0.01 to 1 weight percent of at least one soluble surface tension reducing compound;

C) from 0.0001 to 0.5 weight percent of at least one simethicone;

D) from 15 to 98 weight percent water; and

E) 70 weight percent or less of one or more volatile organic compounds.

11. The aqueous hair styling composition of claim 10, wherein the acrylic hair fixative resin comprises from 1) 5 to 95 weight percent of at least one $C_1$ to $C_8$ alkyl (meth) acrylate monomer, 2) from 2 to 70 weight percent of at least one hydroxyalkyl (meth)acrylate monomer, and 3) from 2 to 50 weight percent of at least one $C_3$ to $C_8$ monoethylenically unsaturated monocarboxylic acid monomer, based on the total weight of monomer.

12. The aqueous hair styling composition of claim 10, wherein: the acrylic hair fixative resin comprises from 5 to 71 weight percent of at least one $C_1$ to $C_3$ alkyl methacrylate monomer; from 2 to 67 weight percent of at least one $C_2$ to $C_5$ alkyl acrylate monomer; from 2 to 26 weight percent of at least one hydroxyalkyl (meth)acrylate monomer; and from 2 to 30 weight percent of at least one $C_3$ to $C_8$ monoethylenically unsaturated monocarboxylic acid monomer, based on the total weight of monomer.

13. The aqueous hair styling composition of claim 10, wherein the soluble surface tension reducing compound is selected from the group consisting of dimethiconecopolyols, panthenol, fluorosurfactants, glycerin POE, PPG 28 Buteth 55, PEG 75 lanolin, octoxynol-9, PEG-25 hydrogenated castor oil, polyethylene glycol 25 glyceryl trioleate, oleth-3 phosphate, PPG-5-ceteth-10 phosphate, PEG-20 methyl glucose ether, glycereth-7-triacetate, and glycereth-7-benzoate.

14. The aqueous hair styling composition of claim 10, further comprising: at least one propellant.

15. A method for reducing beading on hair from an aqueous hair styling composition, comprising: adding to the aqueous hair styling composition from 0.0001 to 0.5 weight percent of at least one simethicone;

wherein the aqueous hair styling composition is applied to the hair by a spray and the aqueous hair styling composition comprises from 1 to 15 weight percent of at least one acrylic hair fixative resin; from 0.01 to 1.0 weight percent of at least one soluble surface tension reducing compound; from 15 to 98 weight percent water; and 70 weight percent or less of one or more volatile organic compounds.

* * * * *